United States Patent [19]

Kozakura et al.

[11] Patent Number: 5,271,894
[45] Date of Patent: Dec. 21, 1993

[54] CHEMILUMINESCENT ANALYZER

[75] Inventors: Masaru Kozakura, Kyoto; Shingo Sumi, Moriyama; Hiroaki Matsuhisa, Kyoto; Hideyuki Miki, Kameoka, all of Japan

[73] Assignee: Shimadzu Corporation, Kyoto, Japan

[21] Appl. No.: 20,394

[22] Filed: Feb. 22, 1993

[30] Foreign Application Priority Data

Feb. 27, 1992 [JP] Japan .................. 4-78686

[51] Int. Cl.$^5$ .................................. G01N 21/76
[52] U.S. Cl. ....................... 422/52; 422/82.05; 422/86; 436/172; 73/864.81; 73/864.85; 73/864.91
[58] Field of Search ............ 422/52, 82.05, 86; 436/172; 73/864.81, 864.85, 864.91

[56] References Cited

U.S. PATENT DOCUMENTS

| | | |
|---|---|---|
| 3,692,485 | 9/1972 | Neti et al. ........................... 422/52 |
| 3,734,691 | 5/1973 | Kukla et al. ........................ 422/52 |
| 3,746,514 | 7/1973 | Colvin et al. ...................... 422/52 |
| 4,018,562 | 4/1977 | Parks et al. ....................... 422/52 |
| 4,193,963 | 3/1980 | Bruening et al. .................. 422/52 |
| 4,236,895 | 12/1980 | Stahl ................................. 422/52 |
| 4,657,744 | 4/1987 | Howard ............................. 422/52 |
| 4,765,961 | 8/1988 | Schiff et al. ....................... 422/52 |
| 5,082,628 | 1/1992 | Andreotti et al. ............... 422/82.08 |

*Primary Examiner*—James C. Housel
*Assistant Examiner*—N. Bhat
*Attorney, Agent, or Firm*—Oliff & Berridge

[57] ABSTRACT

In a chemiluminescent analyzer for measuring a concentration of an object gas in a sample gas by mixing the sample gas with 5 a reaction gas and measuring light generated in a chemical reaction between the object gas and the reaction gas, the two gases flow through a double tube composed of an outer tube and an inner tube, and are mixed at the end of the tubes. The end of the inner tube is closed, and one or more outlets are provided at the side wall of the inner tube near the closed end. The flow of the gas coming out of the inner tube through the outlet or outlets crosses the flow of the gas in the outer tube, which enhances the mixture of the two gases and increases the chance of reaction between the object gas and the reaction gas. Since the flow of the mixed gas is directed toward the inner wall of the outer tube, the solid or liquid reaction product between the impurities in the sample gas and the reaction gas precipitates on the inner wall of the outer tube, not on a transparent glass plate separating the gases and the photometer for measuring the reaction emission (light).

7 Claims, 4 Drawing Sheets

CHEMILUMINESCENT ANALYZER

The present invention relates to a chemiluminescent analyzer which measures a concentration of object gas in sample gas by measuring the light generated by the chemical reaction between the object gas and reaction gas.

BACKGROUND OF THE INVENTION

Combustion in an industrial furnace or combustion in an automobile engine produces nitrogen oxide gas, NOx, which includes nitrogen monoxide (NO) and nitrogen dioxide ($NO_2$). Since it is harmful to humans, it is important to measure the concentration of NOx in the emission gas or in the atmosphere. One of the apparatuses for measuring the NOx concentration is the chemiluminescent analyzer.

A chemiluminescent analyzer for measuring concentration of NO is illustrated using FIG. 1. Sample gas taken from the emission gas or from the atmosphere is mixed with reaction gas including ozone ($O_3$) in a reaction space of the chemiluminescent analyzer 10, where NO and $O_3$ chemically react to generate light. The light generated by the reaction is measured by a photometer of the chemiluminescent analyzer 10, whereby the concentration of the NO in the sample gas is calculated. Concentration of ammonia ($NH_3$) and nitrogen dioxide ($NO_2$) can be similarly measured by converting them to NO beforehand in a separate reaction chamber.

The reaction space of a conventional chemiluminescent analyzer 10 is detailed in FIG. 7. A double tube composed of an outer tube 51 and an inner tube 52 opens against the photometer 57 (e.g., a photo-multiplier or a photodiode) with a transparent glass plate 56 between them. The end of the inner tube 52 is set withdrawn from the end of the outer tube 51 with respect to the photometer 57. The sample gas 13 coming through the inner tube 52 and the reaction gas 14 coming through the outer tube 51 (precisely saying, between the outer tube 51 and the inner tube 52) meet at a space 55 formed by the wall of the outer tube 51 and the end of the inner tube 52. The NO in the sample gas 13 and the $O_3$ in the reaction gas 14 react as

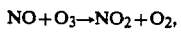

$$NO+O_3 \rightarrow NO_2+O_2,$$

and generate light, which is received and measured by the photometer 57.

A problem about the structure is that the sample gas 13 and the reaction gas 14 do not mix well in the reaction space 55 because they come there in the same direction. Therefore the efficiency of the emission of light from the reaction is low, and the linearlity between the concentration of the object gas (NO) and the measured amount of light is poor. If the end of the inner tube 52 is further withdrawn from the end of the outer tube 51 (i.e., if the distance L2 is increased) to make a larger mixing space 55 and thus to obtain a better mixture, the site of reaction (i.e., the site of generation of light) becomes farther from the photometer 57, which also lowers the measurement efficiency.

Another problem is that, if impurity gas such as ammonia ($NH_3$) or chlorine ($Cl_2$) is included in the sample gas, the reaction with ozone produces precipitation deposit on the transparent glass plate 56 and obscures it.

SUMMARY OF THE INVENTION

According to the present invention made for addressing the problems, a chemiluminescent analyzer (for measuring a concentration of an object gas in a sample gas by mixing the sample gas with a reaction gas and measuring light generated in a chemical reaction between the object gas and the reaction gas) includes:

a) a photometer for measuring the light;
b) an outer tube, for providing either one of the sample gas or the reaction gas, having an open end opposing the photometer;
c) an inner tube placed in the outer tube, for providing the other gas, and having a closed end and one or more outlets at the side wall near the closed end; and
d) a transparent plate placed between the photometer and the open end of the outer tube.

In the above structure, the flow of the gas coming out of the inner tube through the outlet or outlets crosses the flow of the gas in the outer tube. This enhances the mixture of the two gases and increases the chance of reaction between the object gas and the reaction gas. Since the flow of the mixed gas is directed toward the inner wall of the outer tube, the solid or liquid reaction product between the impurities in the sample gas and the reaction gas precipitates on the inner wall of the outer tube, not on the transparent plate.

Since the invention does not depend on the kind of the reacting gases, any kind of combination, other than NO and $O_3$ used in the explanation of the background, that generates light through the reaction is applicable to the present invention.

DETAILED DESCRIPTION OF PREFERRED EMBODIMENTS

Figure 1:
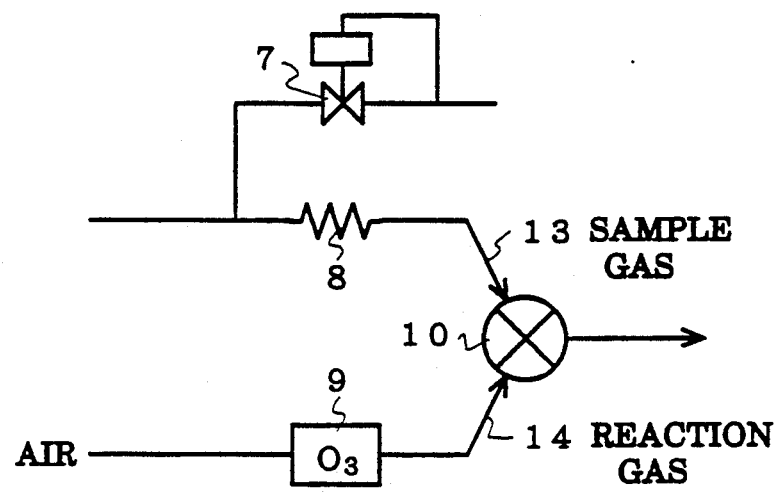
FIG. 1 is a circuit diagram of a measurement system using a chemiluminescent analyzer.

A NO measurement system using a chemiluminescent analyzer according to the present invention is now described. As shown in FIG. 1, sample gas 13 taken from exhaust gas of an industrial furnace, for example, and including NO is introduced to the chemiluminescent analyzer 10 via a flow resistance 8. Reaction gas 14 is produced from the air by an ozone ($O_3$) generator 9, and is also introduced to the chemiluminescent analyzer 10. A flow resistance 8 is provided in the sample gas line, and the excessive sample gas is drained through a relief valve 7. Concentration of ammonia ($NH_3$) and nitrogen dioxide ($NO_2$) in the sample gas can be measured with this system by converting them to NO beforehand in a separate reaction chamber.

Figure 2:
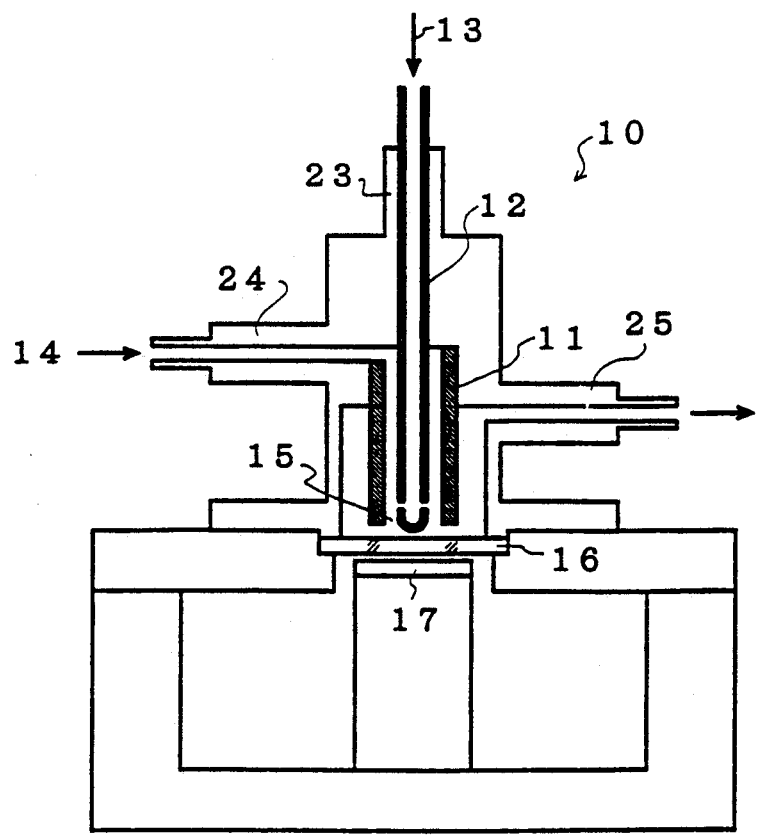
FIG. 2 is a vertical cross-sectional view of a chemiluminescent analyzer as the first embodiment of the present invention.

As shown in FIG. 2, the sample gas 13 enters the chemiluminescent analyzer 10 from a top entrance 23 and flows down to a reaction space 15 through an inner tube 12. The reaction gas 14 including a known concentration of ozone generated by the ozone generator 9 enters the chemiluminescent analyzer 10 from a side entrance 24 and also flows down to the reaction space 15 through an outer tube 11. The inner tube 12 runs coaxially in the outer tube 11 and the two gases 13 and 14 do not meet until at the reaction space 15. When they meet, NO in the sample gas 13 and $O_3$ in the reaction gas 14 react chemically as explained above and generate light, which is observed by a photometer 17 placed below the reaction space 15. A transparent glass plate 16 separates the gases and the photometer 17. The mixed gas goes out of the chemiluminescent analyzer 10 through a side exit 25.

Figure 3A:
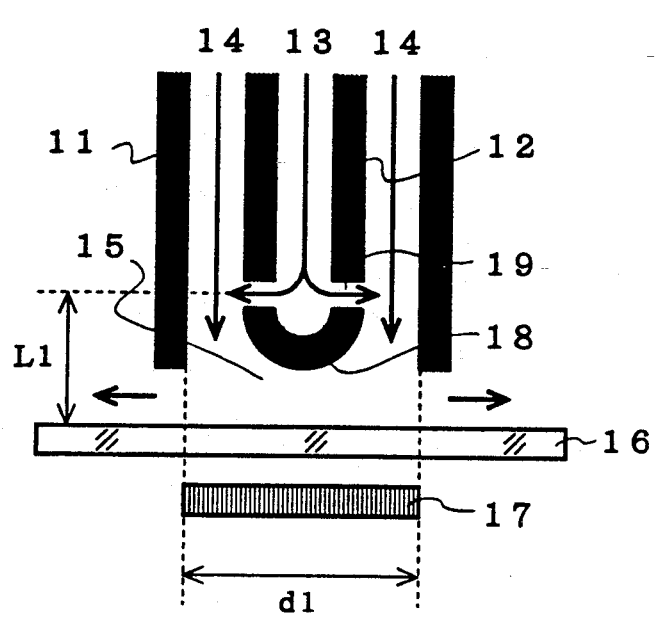
FIG. 3A is a vertical cross-sectional view of a reaction space and the surroundings of the first embodiment.
Figure 3B:
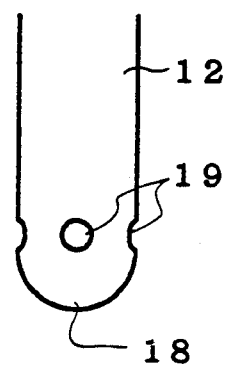
FIG. 3B is a side view of the inner tube.
Figure 7:
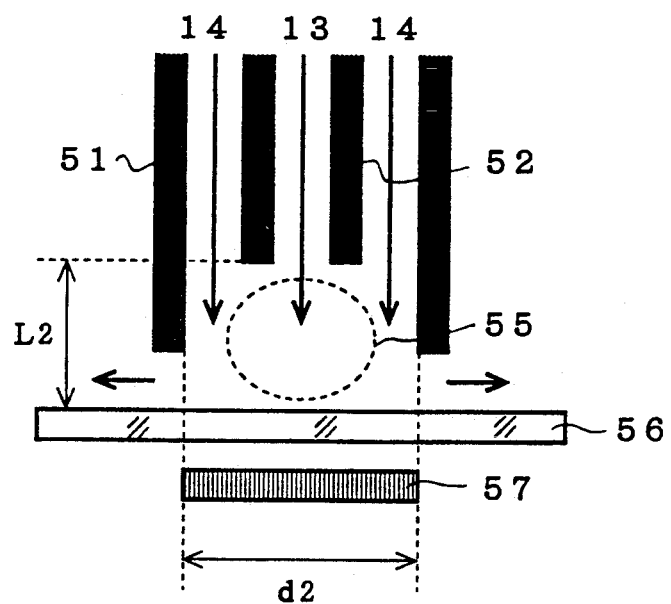
FIG. 7 is a vertical cross-sectional view of the reaction space and the surroundings of a prior art chemiluminescent analyzer.

The reaction space 15 of the chemiluminescent analyzer 10 is detailed in FIGS. 3A and 3B. The bottom end 18 of the inner tube 12 is closed, and four outlet holes 19 are provided in the side wall of the inner tube 12 near the bottom end 18. In the present embodiment, the four holes 19 are placed equally around the periphery of the inner tube 12, but the position or the number of the holes 19 is arbitrary. Owing to the direction of the axis of the side holes 19, the flow of the sample gas 13 coming out of the inner tube 12 perpendicularly crosses the flow of the reaction gas 14 in the outer tube 11. The cross-flow of the two gases 13 and 14 in the reaction space 15 enhances the mixture of the two gases 13 and 14, and increases the chance of encounter of the entire NO content of the sample gas 13 with the $O_3$ in the reaction gas 14. Thus the efficiency of the chemical reaction of the NO and $O_3$ is increased, and the sensitivity of the chemiluminescent analyzer is improved. Actually the sensitivity of the present embodiment is four times greater than that of the prior art chemiluminescent analyzer shown in FIG. 7. The proportionality (linearity) of the amount of light measured by the photometer 17 to the concentration of NO in the sample gas 13 is also ensured.

Since, as explained above, the two gases 13 and 14 are forced to collide by the tube structure of the present embodiment, no large mixing space (reaction space) is necessary. This allows the shorter distance L1 between the end 18 of the inner tube 12 and the photometer 17, and the smaller inner diameter d1 of the outer tube 11, compared to those L2 and d2 of the prior art chemiluminescent analyzer shown in FIG. 7. The smaller dimensions allows the use of a smaller photometer 17 and provides better photo-measurement efficiency, which also improves the sensitivity of the concentration measurement.

The liquid or solid products of the reaction between the impurity components of the sample gas 13 and $O_3$; in the reaction gas 14 precipitates on the inner wall of the outer tube 11 in the present embodiment. Thus the transparent glass plate 16 in front of the photometer 17 remains clear and the high sensitivity of the measurement is maintained for a long time.

Figure 4:
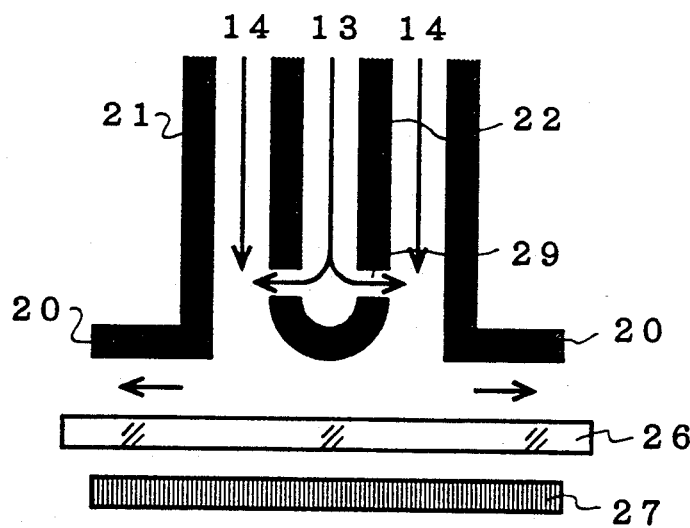
FIG. 4 is a similar view of the second embodiment of the present invention.
Figure 5:
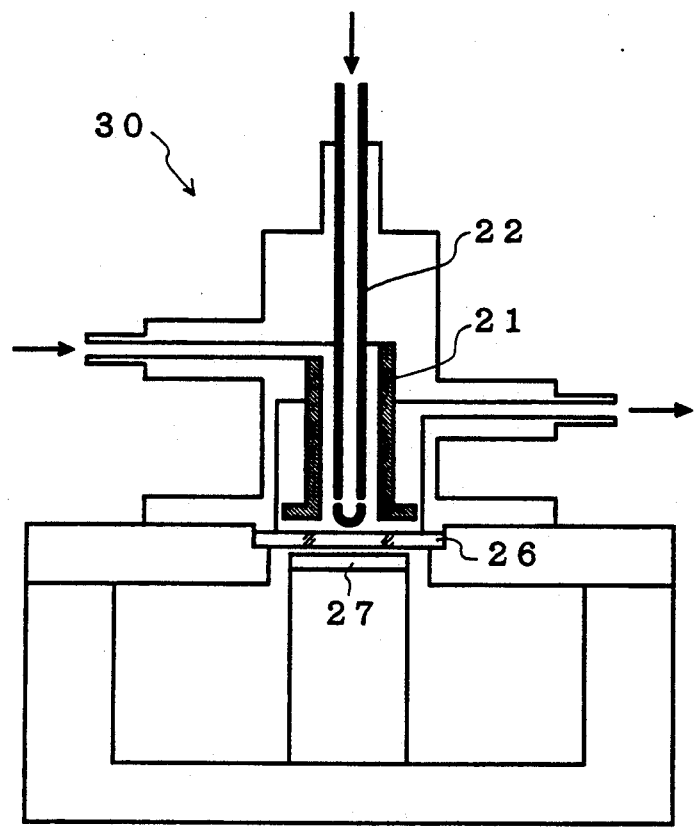
FIG. 5 is a vertical cross-sectional view of a chemiluminescent analyzer of the second embodiment.

Another embodiment of the present invention is now described referring to FIGS. 4 and 5. In the present embodiment, as shown in FIG. 4, a flange 20 is provided to the outer tube 21, extending externally from the bottom end of the outer tube 21 and parallel to the glass plate 26. The lower surface of the flange 20 is made reflective, and the light receiving area of the photometer 27 is made broader to correspond to the flange 20. After the sample gas 13 and the reaction gas 14 are mixed at the exit of the holes 29 of the inner tube 22, the mixed gas flows through the space between the flange 20 and the glass plate 26 before evacuated from the exit of the chemiluminescent analyzer 30. By this structure, more amount of reaction occurs in front of the photometer 27 and more amount of light enters the photometer 27. In addition to that, owing to the reflective lower surface of the flange 20, the amount of measured light is further increased. Thus, in the present embodiment, the sensitivity is increased and the proportionality (linearity) of the measurement is enhanced.

Figure 6:
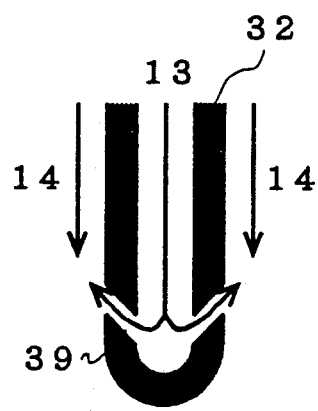
FIG. 6 is a vertical cross-sectional view of a variation of an inner tube.

A variation of the outlet holes of the inner tube is shown in FIG. 6. In this case, the axes of the holes 39 are tilted backward with respect to the axis of the inner tube 32 (and the outer tube), whereby the direction of the flow of the sample gas 13 is more against than perpendicular with respect to the direction of the flow of the reaction gas 14 when they meet. This provides stronger mixing of the two gases 13 and 14 and thus better efficiency of the measurement.

What is claimed is:

1. A chemiluminescent analyzer for measuring a concentration of an object gas in a sample gas by mixing the sample gas with a reaction gas and measuring light generated in a chemical reaction between the object gas and the reaction gas, the chemiluminescent analyzer comprising:

a) a photometer for measuring the light;
    b) an outer tube, means for providing either one of the sample gas or the reaction gas, to said outer tube, said outer tube having an open end opposing the photometer;
    c) an inner tube placed in the outer tube, means for providing the other gas, to said inner tube, aid inner tube having a closed end and one or more outlets at the side wall near the closed end; and
    d) a transparent plate placed between the photometer and the open end of the outer tube and spaced from said open end.

2. The chemiluminescent analyzer according to claim 1, where the axis of the outlet or outlets of the inner tube is perpendicular to the axis of the inner tube and the outer tube.

3. The chemiluminescent analyzer according to claim 1, where the axis of the outlet of the inner tube is tilted backward with respect to the direction of the flow of the gas in the outer tube.

4. The chemiluminescent analyzer according to claim 1, where the inner tube has four outlets.

5. The chemiluminescent analyzer according to claim 1, where a flange extending externally and parallel to the transparent plate is attached to the open end of the outer tube.

6. The chemiluminescent analyzer according to claim 5, where a surface of the flange facing the photometer is reflective.

7. The chemiluminescent analyzer according to claim 6, where the area of the light receiving face of the photometer corresponds to the area of the flange.

* * * * *